United States Patent [19]

Lindsey

[11] 4,263,907

[45] Apr. 28, 1981

[54] RESPIRATOR NEBULIZER

[76] Inventor: Joseph W. Lindsey, 2045 Ribbon La., Salt Lake City, Utah 84117

[21] Appl. No.: 38,657

[22] Filed: May 14, 1979

[51] Int. Cl.[3] .......... A61M 16/00

[52] U.S. Cl. .......... 128/200.18; 128/200.21; 128/205.24; 261/DIG. 65; 239/338

[58] Field of Search .......... 128/200.18, 200.21, 128/205.24; 261/DIG. 65; 239/338

[56] References Cited

U.S. PATENT DOCUMENTS

| | | | |
|---|---|---|---|
| 3,945,378 | 3/1976 | Paluch | 128/200.18 X |
| 4,014,382 | 3/1977 | Heath | 261/DIG. 65 |
| 4,084,587 | 4/1978 | Lindsey | 128/200.18 |

*Primary Examiner*—Henry J. Recla

*Attorney, Agent, or Firm*—M. Reid Russell

[57] ABSTRACT

An improved respirator nebulizer for introducing a water and/or medication aerosol into a flow from a respirator to a patient's respiratory system. The present invention includes a manifold body, wherethrough is passed a demand respirator low pressure main flow to a patient, and includes ducting for passing a high pressure nebulizer flow from the respirator to break up liquid from and within a cup reservoir that is scoured from that reservoir into an aerosol and encapsulated into the main flow. The manifold body, its component elements and the cup reservoir are all preferably formed by conventional molding methods and equipment, with the manifold body and component assemblies intended to be disposable after short usage or, alternatively, can be constructed to be sterilized for additional usage, with cup reservoir intended to hold a pre-measured and mixed liquid and could be disposable after a single use. The cup reservoir is arranged to be separately installed and sealed to an appropriate seat formed on the manifold body, with either the cup reservoir lip or seat incorporating grooving therein that, when the cup reservoir is attached to the manifold body, serves as liquid transport lines and nozzles wherethrough liquid from the cup reservoir is passed and sprayed. The nozzle flows impinge on or strike one another, breaking the sprays into fine particulate aerosol that is scoured from the cup reservoir by that high pressure flow and moved into the main flow.

The manifold preferably incorporates a two position mode valve that, in one position, passes the high pressure flow to both the nebulizer portion and to an exhalation valve, and in the other mode valve position channels the high pressure flow to perform nebulization functions only, which mode valve positioning is dependent upon the type of respirator employed with the present invention, the present invention being suitable for use with the most common Bird ® and Bennett ® respirators.

30 Claims, 12 Drawing Figures

RESPIRATOR NEBULIZER

BRIEF DESCRIPTION OF THE INVENTION

1. Field of the Invention

The present invention relates to respirator nebulizers for use with a conventional respirator, in clinical or home inhalation therapy treatment, for humidifying and medicating a respirator low pressure main flow.

2. Prior Art

Respirator nebulizers for creating a fine particle liquid aerosol, of water and/or medication, for mixing with a main flow from a conventional respirator for inhalation by a patient into his respiratory system are, of course, well known. Examples of such earlier devices are shown in a patent by Seeler, U.S. Pat. No. 3,083,707, with manifold type nebulizer systems shown in patents by Enfield and Huston, U.S. Pat. Nos. 3,874,379 and 3,903,884. In recent times devices for performing such oxygen humidifying have been manufactured for disposal after patient use. It has been found by hospitals that to provide a patient with appliances that are exclusively his during his stay in such a facility and to dispose of them after he leaves has cut down or limited the need for sterilization facilities and more importantly reduced or limited cross-infection between patients when sterilization was not achieved. It has been found in practice that it is less expensive to purchase and dispose of such appliances after each patient use than to provide sterilization thereof. Examples of disposable respirator nebulizers are shown in a patent by Havstad, U.S. Pat. No. 3,826,255, and in an earlier invention of the present inventor, U.S. Pat. No. 3,664,337. Examples of the nebulizing devices that were not necessarily disposable are also shown in patents by Bird, et al., Takaoka, and Brown, U.S. Pat. Nos. 3,172,406; 3,580,249 and 3,724,454.

While the earlier cited patent by the present inventor is a significant breakthrough in patient care, that device and the device of the Havstad U.S. Pat. No. 3,826,255, suffer from similar problems in that their use, over a period of time, may result in a patient being reinfected by his own germs, as those devices do not lend themselves to adequate cleaning. The present invention, unlike the above cited devices and any device within the knowledge of the inventor, provides smooth internal surfaces within a manifold body portion thereof and utilizes a separate cup reservoir attachable therewith. The cup reservoir can contain a pre-measured and mixed solution and is preferably disposed of after a single treatment.

The cup reservoir, additional to providing a disposable container accommodating a pre-mixed solution, is unique in that by appropriate grooves formed therein, and without additional parts or elements, it performs nebulizing functions. Specifically, the cup reservoir lip area and/or seat portion of the manifold body to which the cup attaches incorporate grooves therewith that, when the cup reservoir is in sealing engagement with the seat, act as fluid transfer lines and nozzles through which the cup reservoir's contents, when pressurized, are passed. The formed nozzles oppose each other such that discharges therefrom strike one another, breaking the liquid streams into a small particle aerosol that is passed into and mixed with a main stream low pressure flow from a respirator to a patient. While other prior art devices such as those shown in patents by Babington and Glenn, U.S. Pat. Nos. 3,864,326 and 4,007,238 have shown fluid streams passed through nozzles striking one another to produce an aerosol, none have involved grooves like that of the present invention that also provides, unlike known prior devices, a simplified assembly utilizing minimum parts, simplifying its manufacture and assembly.

Additionally, while the device of the Havstad Patent, U.S. Pat. No. 3,826,255, shows an arrangement for operating a nebulizer with the two most common respirator configurations, i.e., configurations known as the Bird ® and Bennett ® modes, neither it or any device within the knowledge of the inventor employs a simple valve configuration and internal ducting like that of the present invention to provide for mode switching.

The present invention is therefore believed to be unique from any known prior art devices and a significant improvement over respirator nebulizers currently known and in use.

SUMMARY OF THE INVENTION

It is the principal object of the present invention in a respirator nebulizer to provide a device for injecting an aerosol of fine liquid particles into a main respirator flow, the nebulizer having a minimum of component parts that can be formed by conventional injection and molding processes for press-fitting together.

Another object of the present invention is to provide a respirator nebulizer that is inexpensive to produce for use by a single patient during his stay at a hospital.

Another object of the present invention is to provide a respirator nebulizer that incorporates a nebulizer portion consisting of lines and nozzles formed by appropriately grooving the lip or seat area of a detachable cup reservoir portion and connected to a high pressure source.

Another object of the present invention is to provide a respirator nebulizer that can be used with both configurations of major respirator devices, specifically, respirators operating in what is commonly known as Bird ® and Bennett ® modes, providing thereby a universal respirator nebulizer.

Still another object is to provide a respirator nebulizer that can be switched for use in either the Bennett ® or Bird ® modes by appropriate movement of a simple two position mode valve.

Still another object is to provide a respirator nebulizer that includes a manifold body formed to provide a convenient hand grip that will not interfere with the nebulizer operation and minimizes a torque transferred to the patient's hand by the weight of a tubing assembly connected thereto to reduce patient fatigue and discomfort.

Still another object is to provide a device that will nebulize liquid into an aerosol of different size particles that may or may not contain medication and will encapsulate that aerosol into a main respirator flow, which device is inexpensive to fabricate, preferably by molding methods, and has few component parts with smooth internal surfaces to facilitate cleaning thereof.

The principal features of the present invention in a respirator nebulizer include a manifold body including internal respirator and patient main flow conduits formed at a ninety degree angle with one another. This arrangement provides a convenient patient hand-grip at the respirator flow conduit with a mouth-piece secured to the open end of a patient flow conduit. The manifold body, in addition to passing a main low pressure respirator flow, is arranged to receive a respirator high pressure nebulizer flow through a two-position mode valve. The mode valve in one position divides the high pressure flow to nebulize a liquid into an aerosol in a cup reservoir portion and move and mix that aerosol into the main flow, and uses the other portion of that high pressure to operate an exhalation valve arranged in the manifold body. When the mode valve is switched to its other position, the high pressure flow will be used for liquid nebulizing only. The manifold body includes straight passageways therein to facilitate cleaning so as to inhibit bacteria growth.

The above mentioned cup reservoir is intended for a single use only and is arranged for securing in sealing engagement to an appropriate seat formed on the manifold body. The cup reservoir is preferably prefilled with liquid and medication, as desired, for attachment to the manifold by an appropriate latch mechanism, the cup lip sealing to the seat. The cup lip face that engages the seat or the seat itself is formed with grooves therein that serve, when the cup is sealed to the seat, as liquid transfer lines and opposing nozzles. So arranged, when a high pressure flow is directed appropriately into the cup reservoir, the liquid therein will be forced through the nozzles, spraying therefrom against one another, breaking that liquid into fine particle aerosol. The aerosol is scoured from the cup reservoir and passed by the high pressure flow into the center of the respirator main flow, encapsulating it therein to humidfy and medicate that flow to a patient's respiratory system during inhalation.

As stated above, the respirator nebulizer of the present invention provides an exhalation valve with the manifold body that can, alternatively and dependent upon mode valve positioning, receive a pressure flow through a passage in the manifold body, or can be pressurized by an external line. Thereby, by appropriately positioning the mode valve, the present invention can be operated with a two-feed line respirator, one such arrangement commonly known as a Bird ® mode, or a three-feed line respirator, one such arrangement commonly known as a Bennett ® mode. These configurations, Bird ® and Bennett ®, are the most common respirator configurations and both are operated by patient demand.

The respirator main flow is, of course, a low pressure flow that is controlled by patient demand. Patient exhalation passes through an exhalation valve in the manifold body when the respirator flow is cut off by a patient beginning his exhalation cycle. That patient exhalation is passed out of the manifold body through a discharge port.

Further objects and features of the present invention will become more apparent from the following detailed description, taken together with the accompanying drawings.

THE DRAWINGS

FIG. 1 is a profile perspective view of the respirator nebulizer of the present invention showing a cup reservoir therewith that is releasably secured to a seat formed in a manifold body, and includes a mouthpiece;

FIG. 2, an end plan view of the cup reservoir of the respirator nebulizer of FIG. 1, showing a lip face thereof having grooves formed therein that, when the cup face is sealed against the seat in the manifold body, form transfer lines and opposing nozzles, such that liquid within the cup is transferred and sprayed therethrough, breaking that liquid into the small particles shown;

FIG. 2(*a*), a profile perspective view of the cup reservoir of FIG. 2, and showing a thin cover being removed therefrom;

FIG. 2(*b*), a view like that of FIG. 2(*a*), showing one set of grooves forming transfer lines and a nozzle, the spray therefrom shown impinging or striking against the opposite cup reservoir interior wall to break that liquid into small particles;

FIG. 3, an expanded end view of a cup reservoir seat formed in the manifold body of FIG. 1, showing grooves formed therein that should be taken as being the same as, and functioning like, the grooves formed in the cup reservoir lip of FIG. 2;

FIG. 4, a sectional view taken along the lines 4—4 of FIG. 1, showing the respirator nebulizer manifold body and cup reservoir interiors;

FIG. 5(*a*), a sectional view taken within the lines 5—5 of FIG. 4, showing an exploded view of an exhalation valve arranged in the manifold body shown positioned in a Bennett ® mode of operation;

FIG. 5(*b*), a sectional view taken within the lines 5—5 of FIG. 4, showing an exploded view of the exhalation valve of FIG. 5(*a*) shown positioned in a Bird ® mode of operation; and FIGS. 6(*a*) through (*d*) show sectional views of the mode valve, exhalation valve, exhalation cap, and portions of the manifold body and cup reservoir of FIG. 4 and illustrate patient inhalation and exhalation cycles with, in FIGS. 6(*a*) and 6(*b*), the mode valve positioned in the Bird ® mode, and in FIGS. 6(*c*) and 6(*d*), the mode valve positioned in the Bennett ® mode.

DETAILED DESCRIPTION

Background of the Invention

Figure 1:
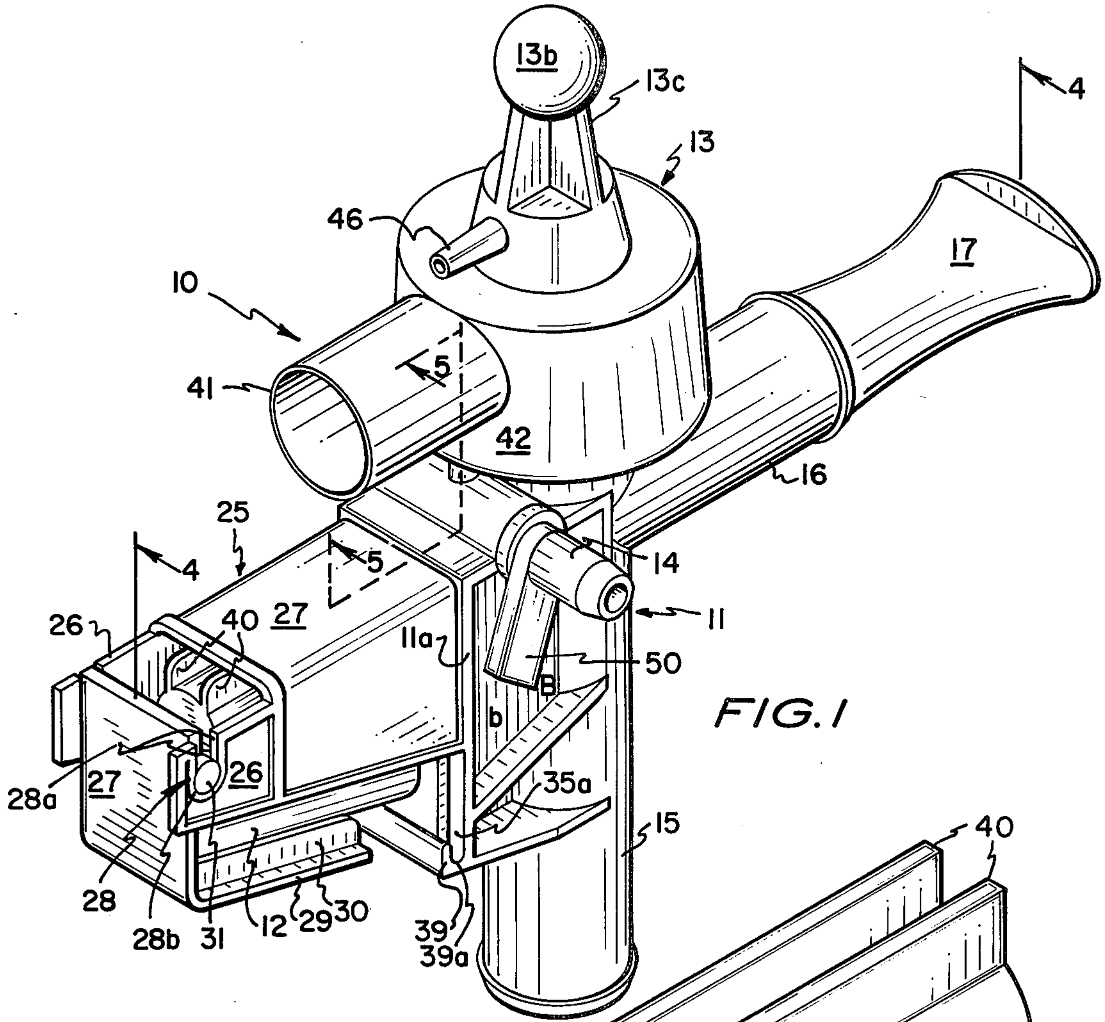

Increasingly over the past few years, short-term and long-term patient care facilities have tended to turn away from sterilization of medical equipment between patient usages to a utilization of disposable equipment. When a patient enters such a facility, he is currently given certain medical items for his personal use, which items are disposed of at his departure. Obviously, this practice has greatly cut down on the needs for sterilization facilities and personnel and has reduced the danger of infecting one patient with the germs of another. However, particularly in the respirator care area where a patient could be on oxygen over a long period of time, it has been found that respirator nebulizers have traditionally been difficult to clean effectively with a patient's own germs tending to reinfect him. The present invention provides a second generation of such disposables and has solved this problem of patient reinfection by providing smooth internal surfaces that lend themselves to cleaning and a cup reservoir that is disposable after each treatment that preferably include grooves therein that function as nebulizer component assembly. Within the cup reservoir an exact pre-measured solution of water and medication is contained for use by removal of a film cover, the grooves preferably formed in the cup reservoir lip acting as transfer lines and opposing nozzles. The solution is sprayed through the nozzles with sufficient velocity that the sprays upon striking one another break the solution into a small particle aerosol that is transferred into a main respirator flow and travels into a patient's respiratory system.

The present invention is a simplified device from past nebulizers whose nebulization components have generally involved numberous parts that remained with the device until it was disposed of. The cup reservoir of the present invention, as it can be manufactured as a single unit separately from the manifold body, greatly simplifies the manufacture of the manifold body portion and assembly thereof. The resulting respirator nebulizer is therefore less costly, more simple to assemble, and will operate more efficiently than former devices to produce greater concentrations of small size fluid particles for injection into a patient's respiratory tract than former devices. Also, it is a universal device in that it can be used in both conventional respirator modes, i.e., the Bennett® and Bird® modes. Further, the present invention, depending upon the materials from which it is manufactured, could be arranged for sterilization and re-use, as desired, and so need not be made to be disposable after a single patient use.

Referring now to the drawings:

The Invention

Figure 4:
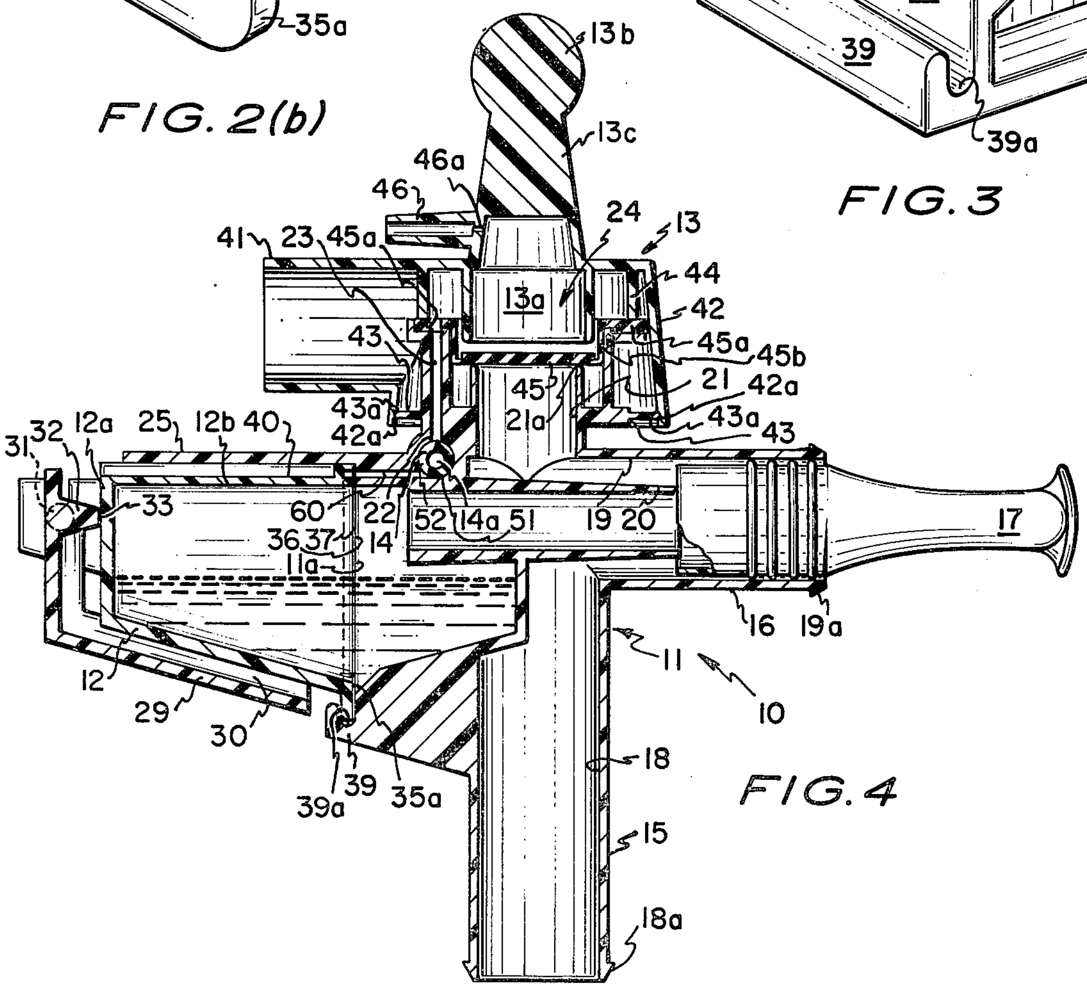

In FIG. 1 is shown a preferred embodiment of an improved respirator nebulizer 10 of the present invention, hereinafter referred to as nebulizer. FIG. 4 shows a cross-section of nebulizer 10 of FIG. 1 illustrating the preferred internal configuration thereof. Shown therein, the nebulizer 10 preferably consists of four assemblies or components that are joined together as will be described later herein. Those components consist of a manifold body 11, a cup reservoir 12, an exhalation cap 13 containing an exhaust valve 24, and a two position pressure mode valve 14 hereinafter referred to as mode valve. The manifold body 11 is preferably formed as a single unit from a plastic material such as a polypropylene, or a like synthetic resin, by injection molding methods. That manifold body 11 preferably consists of a main respirator flow barrel 15, hereinafter referred to as main barrel, and a patient flow barrel 16, hereinafter referred to as patient barrel. The end of the patient barrel 16 connects to a mouthpiece 17 for insertion into a patient's mouth, not shown. The main barrel is connected to a main flow line, not shown, from a conventional respirator, not show, carrying a low pressure flow, preferably oxygen. The respirator, as will be explained in detail later herein, preferably operates on either one or two modes. The first mode is commonly known as a Bird® mode which involves two flows, a low pressure main flow and a high pressure nebulizer flow. The second mode of operation is commonly known as a Bennett® mode which involves three flows, the low pressure main flow, the high pressure nebulizer flow, and a third exhalation operation flow.

In FIG. 4 the respirator barrel 15 is shown as containing a respirator flow channel 18 that connects to and makes a right or normal angle to a patient flow channel 19 formed within patient barrel 16. So arranged, a patient can conveniently hold on to the respirator barrel 15 and connected respirator main flow line, holding the device as a pistol to direct mouthpiece 17 into his mouth, not shown. In FIG. 4 a nebulizer flow channel 20 is arranged in the manifold body 11, centered within patient flow channel 19, communicating therebetween and to the interior of cup reservoir 12, for passing, as will be described later herein, and encapsulating an aerosol from cup reservoir 12 into the respirator main flow traveling to a patient.

Arranged within manifold body 11, in communication with the patient flow channel 19, is an exhalation passage 21 that receives patient exhalation passed through mouthpiece 17, that exhalation traveling to atmosphere, as will be described later in detail herein. Formed also in the manifold body 11 is a seat 22 wherein the mode valve 14 is pivotally secured. Communicating with that seat 22 is an exhalation valve passage 23 for transferring an air flow therethrough into a chamber 13*a* above an exhalation valve 24, as will be described in detail later herein, to close off exhalation passage 21 during patient inhalation.

Shown in FIGS. 1 and 4, formed on manifold body 11 and extending from an end 11*a* thereof opposite to mouthpiece 17, is a cup reservoir hood 25, hereinafter referred to as hood. The hood 25 preferably extends outwardly from and partially encircles a flat end 11*a* of manifold body 11. The flat end 11*a* preferably has a cup reservoir seat arranged thereon. Shown in FIG. 1, the hood 25 extends at a normal angle outwardly from manifold body end 11*a*, terminating in parallel latch mounting brackets 26 that extend from either side thereof, with a web 27 extending thereacross. Pivot grooves 28 are formed in each latch mounting bracket to accommodate ends of a pivot 31 of a latch 29, installed therein. Latch pivot 31 is forced along groove side 28*a* into opening 28*b*, journaling the latch 29 thereto. Latch 29 also incorporates stiffeners 30 therewith for adding strength thereto. Shown best in FIG. 4, the latch 29 includes a cam 32 formed therewith alongside pivot 31. Cam 32 incorporates a flat face 33 therewith such that, as shown best in FIG. 4, when the latch 29 is rotated appropriately the edge of that flat face 33 pivots across the cup reservoir bottom 12*a* the cam flat face 33 coming to rest against the cup reservoir bottom 12*a* locking a flat lip 35 of the cup reservoir 12 against a cup reservoir seat 36 that is formed in the manifold body end 11*a*. So arranged, with a gasket 37 arranged between the cup reservoir lip 35 and cup reservoir seat 37 as shown best in FIG. 4, a seal is maintained such that a liquid contained in the cup reservoir 12 will not leak when the nebulizer is turned to the attitude shown in FIGS. 1 and 4. To provide for exact alignment and positioning of the cup reservoir lip to the cup reservoir seat, a dog 39, shown best in FIGS. 1 and 4, is arranged to receive a cup reservoir lip edge 35*a*. So arranged, the cup reservoir is pivoted around edge 35*a* thereof within an open area 39*a* of dog 39 to the attitude shown in FIGS. 1 and 4, moving the cup reservoir lip 35 against the cup reservoir seat 36 and thereafter latch 29 is rotated to the attitude shown in FIGS. 1 and 4 to lock the reservoir cup 12 to the manifold body 11. Stiffeners 40 are preferably arranged along side 12*b* of cup reservoir 12 to strengthen that cup and engage the undersurface of hood 25 to positioning the cup reservoir 12 within the hood 25, providing a third point of contact maintaining the cup reservoir lip 35 exactly positioned against the cup reservoir seat 36.

It should be obvious that the arrangement of hood 25 shown in FIGS. 1 and 4 could be inverted with respect to cup reservoir seat 36, the open area of hood 25 facing upwardly, or appropriate parallel tracks could be included with the cup reservoir seat 36, not shown, to accomodate opposite cup reservoir lip edges slid therein, either of which arrangements would still fall within the scope of this disclosure. So arranged the configurations of the latch 29 and dog 39 would have to be altered appropriately.

Additional to the above-described elements, the manifold body 11 also includes the exhalation valve 24 and parts associated therewith that are arranged within the exhalation cap 13. The exhalation cap 13, as shown best in the sectional view of FIG. 4, preferably includes an exhaust port 41, that is in communication with chamber 13*a* within exhalation cap 13 above the exhalation valve 24. The exhalation cap 13, as shown best in FIGS. 1 and 4, is formed with a post 13*c* and ball 13*b* arranged on top thereof and includes a skirt 42 that extends downwardly therefrom over the exhalation valve seat of the manifold body 11. The skirt 42 is sealed to an edge 43*a* of a plate 43 by forcing it thereover until a groove 42*a*, formed around the skirt interior passes into that plate edge 43*a*. Plate 43, as shown in FIG. 4, extends at a normal angle to the exhalation passage 21.

The exhalation cap 13, like manifold body 11 and cup reservoir 12, is also preferably formed by injection molding methods and techniques, from a suitable synthetic resin such as polypropylene, and is press fit to manifold body 11 as described hereinabove. When exhalation cap 13 is so installed, an end of an internal pier 44, will maintain a rim 45*a* of an inverted top hat diaphragm 45, hereinafter referred to as diaphragm, of exhalation valve 24. So arranged, as shown best in FIG. 4 and FIGS. 6(*a*) through 6(*d*) the diaphragm 45 is maintained at its rim 45*a* to move vertically, to lift off a seat end 21*a* of exhalation passage 21. The diaphragm 45 is thereby moved upwardly, opening the exhalation passage 21 to pass an exhalation flow into exhalation port 41. Functioning of the exhalation valve 24 during inhalation and exhalation cycles, will be described later herein with respect to FIGS. 6(*a*) through 6(*d*).

As stated earlier herein, exhalation valve passage 23 extends from mode valve 14, emptying above diaphragm 45 within chamber 13*a*, in Bird ® mode positioning. The mode valve 14 is closed when in the Bennett ® mode with diaphragm pressurization then supplied by a third pressure line from the respirator, not shown, that connects to a port 46 in the exhalation cap 13 and empties also into the chamber 13*a*. Port 46 when not connected to the respirator in the Bennett ® mode of operation, as when the nebulizer 10 is operating in the Bird ® mode, acts as an exhaust flow control port for exhausting pressure from chamber 13*a*. A constriction 46*a*is preferably provided in port 46 for limiting air flow therethrough. So arranged, when the nebulizer 10 is operating in the Bird ® mode, with the exhalation valve 24 pressurized through line 23, while a pressure bleed will be continuous past constriction 46*a*, there will remain sufficient pressure in chamber 13*a* due to the size of that constriction, to maintain exhalation valve 24 in a sealed attitude during patient inhalation.

Figure 5A:
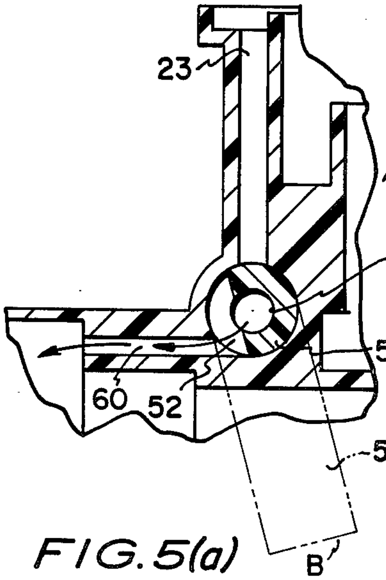
Figure 5B:
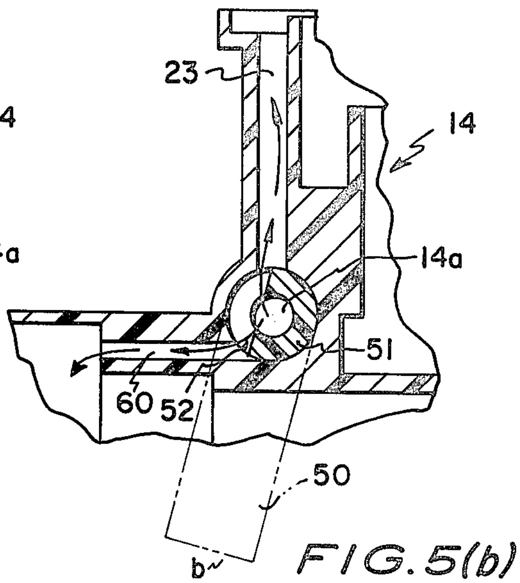
Figure 6A:
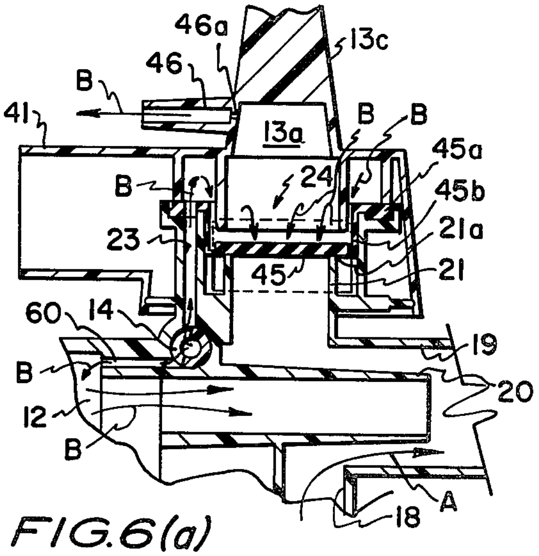
Figure 6B:
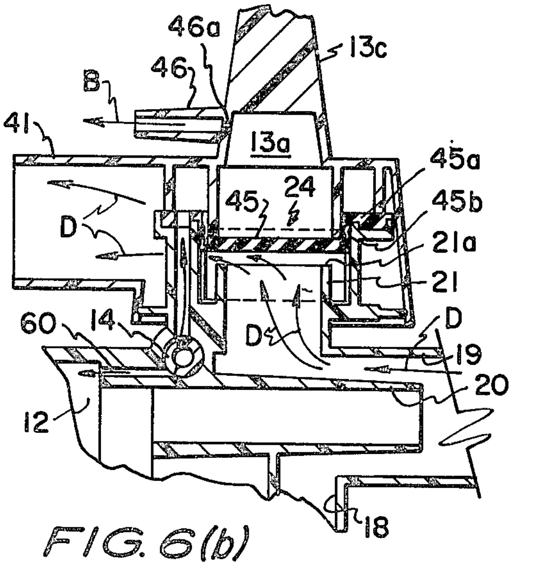
Figure 6C:
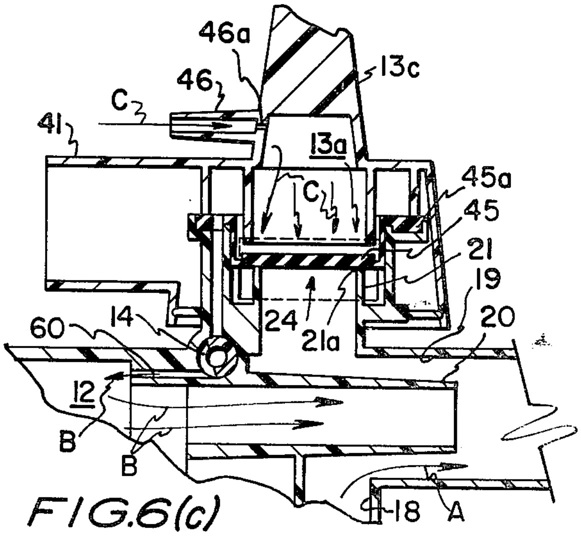
Figure 6D:
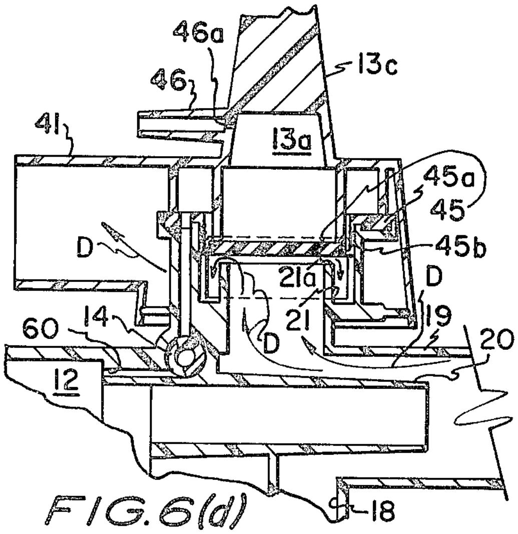

Shown in FIG. 1 and FIGS. 5(*a*) and 5(*b*), mode valve 14 preferably includes a pivot arm 50 arranged therewith that can be moved between a small letter b and a capital letter B. Small "b" is intended to represent the Bird ® mode of respirator operation, with the capital "B" to represent the Bennett ® mode of respirator operation. It should be understood the mode valve is appropriately fitted into seat 22 to be capable of pivoting therein but is sealed to prohibit a pressure flow therearound into passage 23 when turned to the attitude shown in FIG. 5(*a*). Shown in cross-sectional view of FIG. 4, mode valve 14 consists of a rod, dowel, or a like configuration that should be understood to be pivotally mounted within manifold body 11, and is center bored at 14*a* having a portion 52 thereof removed strategic to the opening to the passage 23. Mode valve 14 should be understood to be continuously open to a nebulizer passage 60, and can, with appropriate rotation, move a part of a solid area 51 over the exhalation valve passage 23. The nebulizer and exhalation passages, of course, are offset with one another. So arranged, as shown in FIG. 5(*a*), where the arm 50, shown in broken lines, is rotated to point to the capital "B", that solid area 51 will close off exhalation valve passage 23, prohibiting air flow therethrough. Whereas, as shown in FIG. 5(*b*), with the arm 50, shown in broken lines, moved to the attitude shown by the small letter "b", the high pressure flow entering through 14*a* will pass both through exhalation valve passage 23 and nebulizer passage 60.

Therefore, by a simple movement of arm 50 of mode valve 14, it is possible to switch from the Bird ® mode of respirator operation to the Bennett ® mode. Operation of exhalation valve 24 in relation to the appropriate positioning of mode valve 14 will be explained in greater detail later herein with respect to FIGS. 6(*a*) through 6(*d*).

As stated hereinabove, the nebulizer 10 of the present invention preferably includes four components that are molded and coupled together into the invention. The described mode valve 14, exhalation cap 13 with the exhalation valve 24 therein, of course, once they are fitted to the manifold body 11 are integral to the unit. The cup reservoir 12, however, is intended to be manufactured separately and is for replacement after each treatment. Whereas, the nebulizer 10, less cup reservoir 12, is intended to be replaceable or disposable after a patient has discontinued respirator treatment, and can even be fabricated so as to be capable of being sterilized for re-use by a new patient.

The cup reservoir 12 is intended, as described earlier herein, to be mounted in releasable sealing engagement to a cup reservoir seat 36 formed in end 11*a* of manifold body 11 and provides a capability of containing a desired pre-measured and pre-mixed solution of water and medication therein. Shown in FIG. 2(*a*) the cup reservoir is preferably sealed, as with a film covering 12*c* after filling, which covering is removed prior to attachment to manifold body 11. Obviously, with a solution in the cup reservoir 12 and film 12*c* removed, to install the cup reservoir as shown in FIGS. 1 and 4, it is necessary to tip the manifold body 11 appropriately such that mouthpiece 17 extends vertically. Whereafter, the cup lip 35 can be installed such that the edge 35*a* thereof fits in the opening 39*a* and the latch 29 is rotated to pivot cam flat face 33 into engagement with the cup reservoir end 12*a*. So arranged, the cup reservoir lip 35 is sealed to the cup reservoir seat 36 with gasket 37 therebetween, and the nebulizer 10 can then be pivoted or rotated to the attitude shown in FIGS. 1 and 4.

Figure 2:
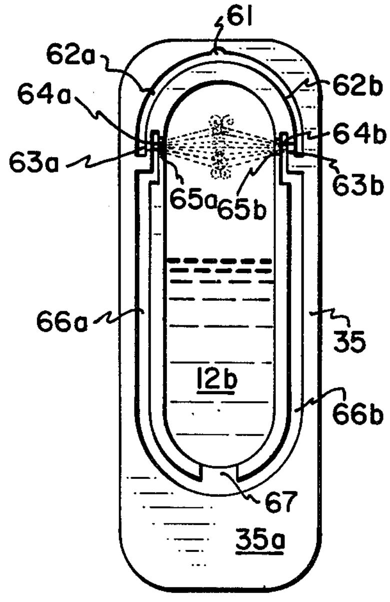
Figure 2A:
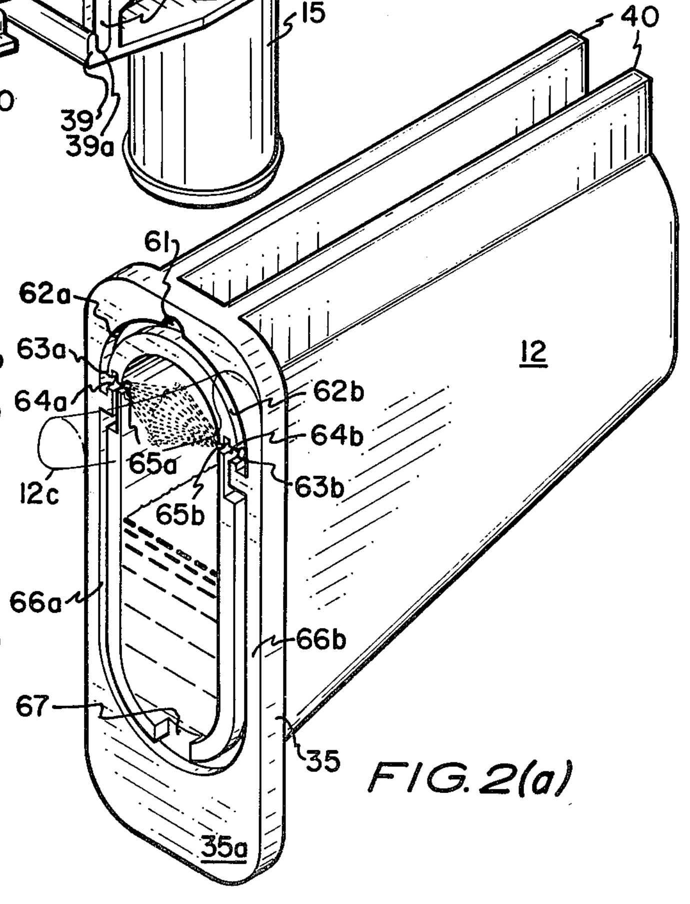
Figure 2B:
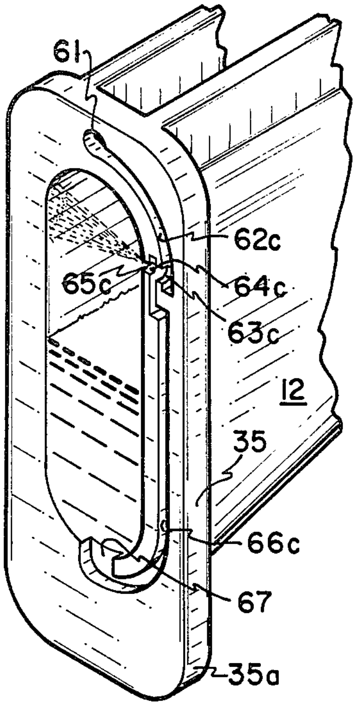

Referring now to FIGS. 2, 2(*a*) and 2(*b*), nebulizing or breaking into a fine particle aerosol of a solution or liquid 12*b* contained within the cup reservoir 12 is preferably provided by formation of liquid flow lines and nozzles as grooves in the lip 35 of cup reservoir 12. Shown in an end view of cup reservoir 12, in FIG. 2, the grooves when sealed against a flat face of cup reservoir seat 36 and gasket 37 form a high pressure receiving port 61 that receives a high pressure flow through passage 60 in manifold body 11. That high pressure flow is divided at port 61, passing through semi-circular grooves 62*a* and 62*b* that extend along the cup reservoir lip 35 and terminate in nozzles 63*a* and 63*b* and operate as high pressure transfer lines. Each nozzle 63*a* and 63*b* has a narrow neck or throat 64*a* and 64*b* formed therein, spreading therefrom into opposing bell-shaped discharge ends 65*a* and 65*b*. Intersecting the nozzle throats 64*a* and 64*b* are fluid transfer lines 66*a* and 66*b* wherethrough liquid 12*b* maintained in cup reservoir 12 is drawn by a pressure differential at the throats 64*a* and 64. So arranged, the high pressure air flow creates a suction at the nozzle throats drawing the liquid from the cup reservoir through opening 67 into the fluid transfer lines 66*a* and 66*b*, into the high pressure flow. The liquid 12*b* is sprayed out from the opposing nozzle bell ends 65*a* and 65*b*, that direct the sprays against one another meeting at a midpoint in the cup reservoir interior. So arranged, a fluid flow picked up through port 67 is sprayed out from nozzle ends 65*a* and 65*b* breaking into a fine particle aerosol. The high pressure passed thereby into the cup reservoir 12 then scours the cup reservoir interior, picking up the aerosol and passing it into the nebulizer passage 20. The nebulizer passage 20 passes the aerosol into the center of the respirator flow, and moving with the respirator flow passing through mouthpiece 17 to the patient. By impacting the spray from one nozzle against the other, the cumulative impact velocity doubles over what it would be with one spray hitting a solid object, thereby creating a large percentage of fine liquid particles, with large particles falling back into the liquid 12*b* within cup reservoir 12. Also, as the velocity of the spray is dependent upon the flow volume through the nozzles and therefore is governed by the geometry of the transfer lines and nozzles, by an appropriate selection or formation of the transfer lines and nozzles the spray velocity can be regulated to produce a desired size of aerosol particles. So arranged, by appropriate coding, as say with different colors, cup reservoirs 12 having certain geometry of transfer lines and nozzles to produce a desired aerosol particle size can be identified. Such color coding could involve different colors of the cup reservoir 12 itself, or as shown in FIG. 2(*a*), by color coding of film 12*c*.

While the above arrangement of two opposing nozzles is preferred, FIG. 2(*b*) shows an alternative grooving of liquid transfer and nozzle arrangement. In this arrangement, a high pressure nebulizer flow enters port 61 in cup reservoir lip 35 from passage 60 and travels into a single semi-circular groove 62*c* that operates as a high pressure transfer line. The flow then enters a single nozzle 63*c* passing through a narrow neck or throat 64*c* thereof and out a bell shaped discharge end 65*c*. Similar to the operation described with respect to FIGS. 2 and 2(*a*), liquid from the cup reservoir is pulled through opening 67 and through a single fluid transfer line 66*c* by a pressure differential created at the narrow neck or throat by the high pressure flow therethrough, mixing with the air flow through throat 64*c*. In this embodiment, however, unlike the embodiment described in FIGS. 2 and 2(*a*), a flow from that nozzle is directed to strike against the opposite cup reservoir 12 interior wall, as shown in FIG. 2(*b*). The discharge from nozzle 63*c* strikes the wall, breaking up the liquid and air flow into a fine particle aerosol, functioning like the arrangements shown and described with respect to FIGS. 2 and 2(*a*). While single and two opposing nozzles 63*a*, 63*b* and 63*c* and the connecting transfer lines as shown herein are preferred, it should be obvious that additional nozzles could be included, which inclusion would still fall within the scope of this disclosure.

Figure 3:
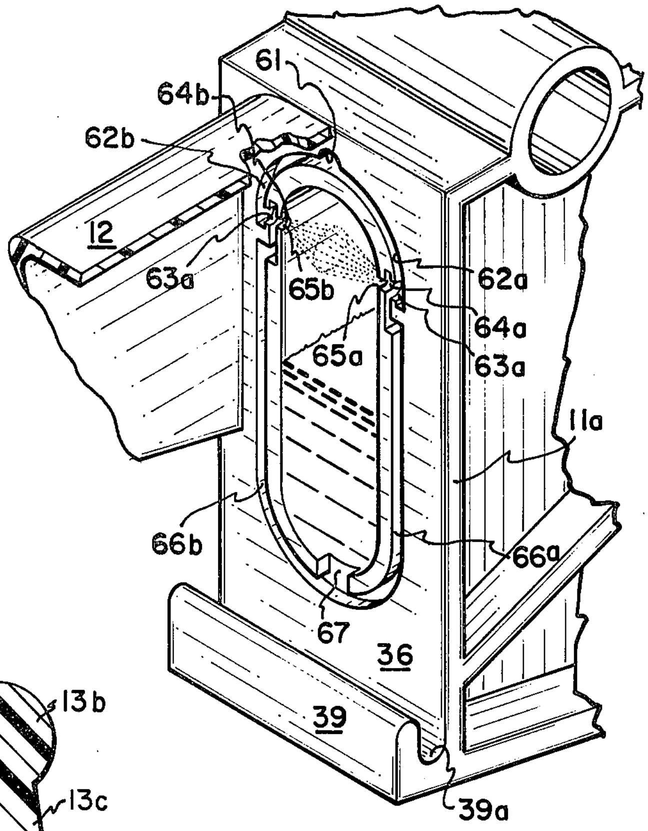

The description hereinabove, with respect to FIGS. 2, 2(*a*) and 2(*b*), shows grooves formed in the lip 35 of cup reservoir 12 with the cup reservoir seat 36 and gasket 37 as flat surfaces. Alternatively, and without departing from the subject matter coming within the scope of this disclosure, the cup reservoir seat 36 in the manifold body end 11*a* could be grooved appropriately. In this configuration, the lip 35 of the cup reservoir 12 would preferably be a smooth flat surface as would gasket 37 to close off said grooves, thereby forming the described transfer lines and nozzles. Nebulizing operations of the arrangement of FIG. 3 should be taken as being exactly like that shown and described with respect to FIG. 2(*a*), and therefore the same numbering has been applied to those grooves as was given to the grooves of FIG. 2(*a*), the grooves of FIG. 3 being a mirror image to the grooves of FIG. 2(*a*).

Operation

With nebulizer 10 arranged in the Bird ® mode, as shown in FIGS. 1, 4 and 5(*b*), a low pressure flow from respirator, not shown, preferably oxygen, travels through respirator flow channel 18 joining and encapsulating the aerosol produced in the cup reservoir 12 as it exits nebulizer flow channel 20. The flown then travels through the patient flow channel 19 and mouthpiece 17 into a patient's respiratory system. The respirator, not shown, produces the main low pressure flow and a high pressure nebulizer flow. The high pressure nebulizer flow travels through mode valve 14, entering through inlet 14*a*, passing, as shown in the arrangement of FIG. 5(*b*), through passage 23 above exhalation valve 24. These flows are controlled by patient demand in that, when a patient inhales, a pressure differential is created at the respirator that operates appropriate valving therein to initiate the described flow. During patient exhalation, when the patient breathes back against the respirator flow, a back pressure is sensed at the respirator that discontinues the flows therefrom. Therefore, the patient controls operations of the respirator, that, in turn, provides the needed flows and controls nebulizer 10 operation.

FIGS. 6(*a*) and 6(*b*) show the nebulizer 10 operated in Bird ® mode of respirator operation, and include arrows that indicate air flow during patient inhalation and exhalation. So arranged, the mode valve 14 is positioned to the Bird ® mode passing a portion of the high pressure flow through passage 23. Shown in FIG. 6(*a* ) therein, the low pressure flow, arrow "A", travels through respirator flow channel 18 and into patient flow channel 19 wherein it is mixed with a flow, arrow "B", coming from cup reservoir 12 that contains an aerosol of fine particles of water and is optionally medicated. Of course, the patient is, at this time, inhaling. Nebulization of the cup reservoir 12 contents is provided by high pressure nebulizer flow, arrow "B", that is shown dividing at mode valve 14, part passing through nebulizer passage 60, the balance passing through exhalation valve passage 23, into chamber 13*a* above diaphragm 45 of exhalation valve 24. The diaphragm 45 is thereby pressed downwardly on the seat area 21*a* of exhalation passage 21, closing that passage off during patient inhalation. Port 46 is open to atmosphere and vents pressure shown by arrow "B". Flow through port 46 is controlled by constriction 46*a* to retain sufficient pressure in chamber 13*a* to hold exhalation valve 24 closed during patient inhalation.

Shown in FIG. 6(*b*), at the time when the patient begins to exhaust gas from his lungs, that back pressure will shut off the respirator, discontinuing the respirator flows, pressure within chamber 13*a*, arrow "D", exhausting through port 46. The patient exhalation travels around nebulizer passage 20, and into exhaust passage 21 elevating diaphragm 45 off from exhaust passage seat 21*a*, the flow traveling out the exhaust port 41. Whereafter, the cycle is repeated.

Referring to FIGS. 6(*c*) and 6(*d*), shown therein are inhalation and exhalation cycles like that described with respect to FIGS. 6(*a*) and 6(*b*) hereinabove, only showing the mode valve 14 of nebulizer 10 turned to operate in the Bennett ® respirator mode. Shown therein, a low pressure flow, arrow "A", from the respirator, not shown, passes through the respirator main flow channel 18 and encapsulates the aerosol coming from the nebulizer flow channel 20, shown as arrow "B", the combined flows traveling to the patient through patient flow channel 19. In this configuration, the high pressure nebulizer flow passes through mode valve 14 and into passage 60 only, to nebulize the contents of cup reservoir 12, as has been hereinbefore described. This respirator arrangement includes a third pressure line coming from the respirator, not shown, identified as arrow "C", that connects to port 46 to pass an air pressure flow into chamber 13*a* above the diaphragm 45 of the exhalation valve 24. Shown in FIG. 6(*c*), that pressure, arrow "C", holds the diaphragm 45 against exhalation passage seat 21*a*, prohibiting air flow therearound during patient inhalation. In the arrangement of FIG. 6(*d*), inhalation has ceased and the patient is exhaling, as sensed at the respirator that shuts off the three flows, with patient exhaust shown as arrow "D". So configured, as was described with respect to FIG. 6(*b*), the exhaust pushes upwardly on the diaphragm 45, elevating it off the exhalation passage seat 21*a*. The patient exhaust then passes out through the exhaust port 41. Any pressure trapped within exhalation chamber 13*a*, that would hold the exhalation valve closed, is bled back along with the patient exhalation through port 46 to the respirator.

As stated earlier herein, the present invention in a nebulizer 10 provides internal surfaces that are essentially smooth for simplifying cleaning thereof and to minimize a danger of bacteria growth therein. The cross-sectional view of FIG. 4 shows that the air flow passages therein are essentially straight with few corners simplifying cleaning thereof, and as cup reservoir 12 is intended to be disposable after each use it could not be a source of bacteria growth, a danger of bacteria growth is thereby minimized.

It should be noted, with reference to FIGS. 4 and 6(*b*) and 6(*d*), that diaphragm 45 is preferably constructed to have the shape of an inverted hat, with upstanding side walls 45*b* that will flex when patient exhalation, arrow "D", is passed therethrough. Diaphragm 45, at rim 45*a* thereof, is sealed within the top portion of exhalation cap 13, prohibiting air passage thereat.

As was stated earlier herein, the present invention is preferably formed by conventional molding methods from a synthetic resin, such as polypropelene, or the like, and the components thereof are preferably force fitted together. Obviously, of course, other materials and assembly techniques could be employed without departing from the subject matter coming within the scope of this disclosure. Further, nebulizer 10 could be formed so as to be capable of being sterilized for additional patient use, as desired. Mouthpiece 17, while not described in detail herein, should be considered to be a standard mouthpiece, fitted to the patient flow channel 19, as shown, or could be slid over the outer surface of the patient flow channel 19 such that flanged ends 19*a* thereof lock within the mouthpiece end. Further, flanged ends 18*a* are shown on the end of respirator flow channel 18 for facilitating connection to the main respirator flow line.

Although preferred embodiments and elements of the nebulizer 10 of the present invention are shown and described herein, it should be understood that the present disclosure is made by way of example only and that variations are possible without departing from the subject matter coming within the scope and spirit of the following claims, which claims I regard as my invention.

I claim:

1. A respirator nebulizer comprising, a manifold body;

means arranged with said manifold body for connection to both intermittent high and low pressure gas flows from a respirator;

first duct means formed in said manifold body to convey said low pressure flow therethrough to a patient's respiratory system;

a cup shaped reservoir;

means with said cup shaped reservoir to communicate with said first duct means and including lip means about its open periphery defining a flat surface and said manifold body including seat means adapted to receive said lip means in sealing engagement therewith, thereby closing said cup shaped reservoir;

means for releasably securing, in sealing engagement, said lip means of said cup shaped reservoir to said seat means of said manifold body;

second duct means formed in said manifold body to pass said high pressure flow to said seat means;

means for nebulizing a liquid within said cup shaped reservoir that includes grooves formed in said flat surface of said cup shaped reservoir lip means, which grooves form, when said lip means is sealingly engaged against said seat means, air and liquid transfer lines and nozzle means, said liquid transfer line communicating the interior of said cup shaped reservoir with said nozzle means, said air transfer line communicating with said second duct means, said nozzle means communicating with both said air and liquid transfer lines such that said high pressure flow aspirates and nebulizes liquid from said reservoir and sprays said nebulized liquid into said first duct means whereby said liquid is broken into a fine particle aerosol which aerosol is scoured by said low pressure flow in said first duct; and means communicating with said first duct means for purging a patient's exhalation.

2. A respirator nebulizer as recited in claim 1, wherein the manifold body is formed to have a ninety degree (90°) bend therein.

3. A respirator nebulizer as recited in claim 1, wherein, the cup shaped reservoir has stiffeners secured along one side thereof.

4. A respirator nebulizer as recited in claim 1 wherein the means for releasably securing the lip means of said cup shaped reservoir to said seat means consists of, housing means extending from said manifold body to receive the cup shaped reservoir;

latch means that is pivotally coupled to said housing means for biasing the cup shaped reservoir against said manifold body, said latch means incorporating a cam that, when said latch means is pivoted appropriately, will engage a bottom surface of said cup shaped reservoir urging said lip means thereof into sealing engagement with said manifold body seat means; and a gasket arranged between the cup shaped reservoir lip means and seat means.

5. A respirator nebulizer as recited in claim 1, wherein, the grooves in said cup shaped reservoir lip means that form a liquid transfer line intersect the throat of the nozzle means such that the high pressure gas flow creates a pressure differential at said throat to draw said liquid therein.

6. A respirator nebulizer as recited in claim 1, wherein said cup shaped reservoir lip means includes, a second set of gas and liquid transfer lines and nozzle means arranged opposite said first set of gas and liquid transfer lines and nozzle means such that said second nozzle means points at the first nozzle means whereby the sprays from each nozzle means will impact one another, breaking the liquid into an aerosol.

7. A respirator nebulizer as recited in claim 1 wherein the spray from said nozzle means strikes a reservoir interior wall opposite thereto.

8. A respirator nebulizer as recited in claim 1, wherein the means for purging a patient's exhalation consists of, an exhalation valve means arranged with said manifold body to close off an exhalation flow passage that is arranged through said manifold body, when the respirator high pressure gas flow is received, said exhalation valve means arranged to open to atmosphere when said respirator high pressure flow is discontinued.

9. A respirator nebulizer as recited in claim 8, wherein the exhalation valve means consists of, a seat arranged across said exhalation flow passage; and a diaphragm means biased over said seat and arranged to be movable vertically off from said seat.

10. A respirator nebulizer as recited in claim 9, wherein the diaphragm means consists of, a top hat shaped diaphragm turned upside down with a rim thereof secured above the exhalation flow passage seat a flat top portion thereof fitting over and biased against said seat, said biasing provided by a flexible diaphragm wall that extends between the rim and flat top; and means for securing said diaphragm rim such that said flat top thereof will extend across said exhalation flow passage seat.

11. A respirator nebulizer as recited in claim 8 further including a means for operating said exhalation valve means comprising, mode valve means arranged in said second duct means of said manifold body and adapted to receive the respirator high pressure flow, said second duct means further communicating with said exhalation valve means, said mode valve means being moveable to a first position, that will pass part of said flow to close off said exhalation valve means and part of said flow to said nozzle means; and into a second position to pass said flow only to said nozzle means; and a vent port connecting to said exhalation valve means to vent pressure therefrom when said high pressure flow is cut off for allowing said exhalation valve means to open to pass patient exhalation therethrough.

12. A respirator nebulizer as recited in claim 11, further including a means for operating said exhalation valve means that consists of, inlet means for communicating a separate respirator high pressure gas flow to said exhalation valve means for passing pressure to close said exhalation valve means when said mode valve means is in said second position and the low pressure and high pressure gas flows are passed.

13. A respirator nebulizer comprising, a manifold body;

means arranged with said manifold body for connection to both intermittent high and low pressure gas flows from a respirator;

first duct means formed in said manifold body to convey said low pressure flow therethrough to a patient's respiratory system;

a cup shaped reservoir;

means with said cup shaped reservoir to communicate with said first duct means and including lip means about its open periphery defining a flat surface and said manifold body including seat means adapted to receive said lip means in sealing engagement therewith, thereby closing said cup shaped reservoir;

means for releasably securing, in sealing engagement, said lip means of said cup shaped reservoir to said seat means of said manifold body;

second duct means formed in said manifold body to pass said high pressure flow to said seat means;

means for nebulizing a liquid within said cup shaped reservoir that includes grooves formed in said flat surface of said seat means, which grooves form, when said lip means is sealingly engaged against said seat means, air and liquid transfer lines and nozzle means, said liquid transfer line communicating the interior of said cup shaped reservoir with said nozzle means, said air transfer line communicating with said second duct means, said nozzle means communicating with both said air and liquid transfer lines such that said high pressure flow aspirates and nebulizes liquid from said reservoir and sprays said nebulized liquid into said first duct means whereby said liquid is broken into a fine particle aerosol which aerosol is scoured by said low pressure flow in said first duct; and means communicating with said first duct means for purging a patient's exhalation.

14. A respirator nebulizer as recited in claim 13, wherein the manifold body is formed to have a ninety degree (90°) bend therein.

15. A respirator nebulizer as recited in claim 13, wherein, the cup shaped reservoir has stiffeners secured along one side thereof.

16. A respirator nebulizer as recited in claim 13 wherein the means for releasably securing the lip means of said cup shaped reservoir to said seat means consists of, housing means extending from said manifold body to receive the cup shaped reservoir;

latch means that is pivotally coupled to said housing means for biasing the cup shaped reservoir against said manifold body, said latch means incorporating a cam that, when said latch means is pivoted appropriately, will engage a bottom surface of said cup shaped reservoir urging said lip means thereof into sealing engagement with said manifold body seat means; and a gasket arranged between the cup shaped reservoir lip means and seat means.

17. A respirator nebulizer as recited in claim 13, wherein, the grooves in said seat means that form a fluid transfer line intersect the throat of the nozzle means such that the high pressure gas flow creates a pressure differential at said throat to draw said liquid therein.

18. A respirator nebulizer as recited in claim 13, wherein said seat means includes, a second set of gas and liquid transfer lines and nozzle means arranged opposite said first set of gas and liquid transfer lines and nozzle means such that said second nozzle means points at the first nozzle means whereby the sprays from each nozzle means will impact one another, breaking the liquid into an aerosol.

19. A respirator nebulizer as recited in claim 13, wherein the spray from said nozzle means strikes a reservoir interior wall opposite thereto.

20. A respirator nebulizer as recited in claim 13, wherein the means for purging a patient's exhalation consists of, an exhalation valve means arranged with said manifold body to close off an exhalation flow passage that is arranged through said manifold body, when the respirator high pressure gas flow is received, said exhalation valve means arranged to open to atmosphere when said respirator high pressure flow is discontinued.

21. A respirator nebulizer as recited in claim 20, wherein the exhalation valve means consist of, a seat arranged across said exhalation flow passage; and a diaphragm means biased over said seat and arranged to be movably vertically off from said seat.

22. A respirator nebulizer as recited in claim 21, wherein the diaphragm means consists of, a top hat shaped diaphragm, turned upside down with a rim thereof secured above the exhalation flow passage seat a flat top portion thereof fitting over and biased against said seat, said biasing provided by a flexible diaphragm wall that extends between the rim and flat top; and means for securing said diaphragm rim such that said flat top thereof will extend across said exhalation flow passage seat.

23. A respirator nebulizer as recited in claim 20 further including a means for operating said exhalation valve means comprising, mode valve means arranged in said second duct means of said manifold body and adapted to receive the respirator high pressure flow, said second duct means further communicating with said exhalation valve means, said mode valve means being moveable to a first position, that will pass part of said flow to close off said exhalation valve means and part of said flow to said nozzle means; and into a second position to pass said flow only to said nozzle means; and a vent port connecting to said exhalation valve means to vent pressure therefrom when said high pressure flow is cut off for allowing said exhalation valve means to open to pass patient exhalation therethrough.

24. A respirator nebulizer as recited in claim 23, further including a means for operating said exhalation valve means that consists of, inlet means for communicating a separate respirator high pressure gas flow to said exhalation valve means for passing pressure to close said exhalation valve means when said mode valve means is in said second position and the low pressure and high pressure gas flows are passed.

25. A respirator nebulizer comprising, a manifold body;

means arranged with said manifold body for connection to both intermittent high and low pressure gas flows from a respirator;

first duct means formed in said manifold body to convey said low pressure flow therethrough to a patient's respiratory system;

a cup shaped reservoir;

means with said cup shaped reservoir to communicate with said first duct means and including lip means about its open periphery defining a flat surface and said manifold body including seat means adapted to receive said lip means in sealing engagment therewith, thereby closing said cup shaped reservoir;

an exhalation valve means arranged in said manifold body;

second duct means formed in said manifold body to pass said high pressure flow to said seat means;

means for nebulizing a liquid within said cup shaped reservoir into a fine particle aerosol including nozzle means that receives said high pressure flow through air transfer lines communicating with said second duct means and liquid from a liquid transfer line communicating with the interior of said cup shaped reservoir such that said high pressure flow aspirates and nebulizes liquid from said reservoir and sprays said nebulized liquid into said first duct means whereby said liquid is broken into a fine particle aerosol, which aerosol is scoured by said low pressure flow in said first duct;

mode valve means arranged in said second duct means of said manifold body and adapted to receive the respirator high pressure flow, said second duct means further communicating with said exhalation valve means, said mode valve means being moveable to a first position, that will pass part of said flow to close off said exhalation valve means and part of said flow to said nozzle means; and into a second position to pass flow only to said nozzle means;

means for releasably securing, in sealing engagement, said lip means to said seat means;

passage means within said manifold body to receive said patient's exhalation and pass it to said exhalation valve means; and a vent port located downstream from said exhalation valve means to vent pressure therefrom when said high pressure flow is cut off allowing said exhalation valve means to open to pass patient exhalation therethrough.

26. A respirator nebulizer as recited in claim 25, wherein, the manifold body is formed to have a ninety degree (90°) bend therein.

27. A respirator nebulizer as recited in claim 25, wherein, the cup shaped reservoir has stiffeners secured along one side thereof.

28. A respirator nebulizer as recited in claim 25 wherein the means for releasably securing the lip means of said cup shaped reservoir to said seat means consists of, housing means extending from said manifold body to receive the cup shaped reservoir;

latch means that is pivotally coupled to said housing means for biasing the cup shaped reservoir against said manifold body, said latch means incorporating a cam that, when said latch means is pivoted appropriately, will engage a bottom surface of said cup shaped reservoir urging said lip means thereof into sealing engagement with said manifold body seat means; and a gasket arranged between the cup shaped reservoir lip means and seat means.

29. A respirator nebulizer as recited in claim 25, wherein the exhalation valve means consists of, a seat arranged around said exhalation flow passage; and a diaphragm means biased over said seat, and arranged to be movable vertically off from said seat.

30. A respirator nebulizer as recited in claim 29, wherein the diaphragm means consists of, a top hat shaped diaphragm, turned upside down, with a rim thereof secured above the exhalation flow passage seat, a flat top portion thereto fitting over and biased against said seat, said biasing provided by a flexible diaphragm wall that extends between the rim and flat top; and means for securing said diaphragm rim such that said flat top thereof will extend across said exhalation flow passage seat.

* * * * *